United States Patent [19]

Djaldetti et al.

[11] Patent Number: 5,242,692
[45] Date of Patent: Sep. 7, 1993

[54] ANTI-METASTATIC FACTOR

[75] Inventors: Meir Djaldetti, Ramat Gan; Pnina Fishman, Herzlia; Benjamin Sredni, Kfar Saba, all of Israel

[73] Assignee: Bar Ilan University, Ramat Gan, Israel

[21] Appl. No.: 550,550

[22] Filed: Jul. 10, 1990

[51] Int. Cl.$^5$ ............... C01C 1/244; A61K 31/44; A61K 3/00
[52] U.S. Cl. .................. 424/548; 530/350; 530/841; 514/356
[58] Field of Search ............. 424/548; 514/356; 530/841, 350

[56] References Cited

U.S. PATENT DOCUMENTS

| | | |
|---|---|---|
| Re. 30,239 | 3/1980 | Kuettner et al. ............ 424/548 |
| 4,042,457 | 8/1977 | Kuettner et al. ............ 424/548 |
| 4,356,261 | 10/1982 | Kuettner ............ 424/548 |
| 4,690,935 | 9/1987 | Taylor et al. ............ 514/356 |
| 4,822,607 | 4/1989 | Balassa et al. ............ 424/548 |
| 4,950,680 | 8/1990 | Taylor et al. ............ 514/356 |

FOREIGN PATENT DOCUMENTS

| | | |
|---|---|---|
| 0159276 | 10/1985 | European Pat. Off. . |
| 5939828 | 3/1984 | Japan ............ 424/548 |
| 0178820 | 9/1985 | Japan ............ 424/548 |

OTHER PUBLICATIONS

Schirmacher V., Tumor Metastases and Cell-Mediated Immunity in a Model System in DBA/2 Mice. V. Transfer of Protective Immunity with H-2 Identical Immune T cells from B10.D2 Mice, Int. J. Cancer, 1979, 233–234.

Nichols, W. W. et al., Characterization of a new Human Diploid Cell Strain, IMR-90., Science, 1977, 196, 60–63.

Primary Examiner—Douglas W. Robinson
Assistant Examiner—Deborah K. Ware
Attorney, Agent, or Firm—Ladas & Parry

[57] ABSTRACT

A factor isolable from muscle tissue or muscle cell culture inhibits proliferation of tumor cells, such as ESB, HT-29 and B-16 F1 cell lines, as well as the peripheral white blood cells of a patient with chronic myeloid leukemia. The active fraction has a molecular weight in the range of 25–30,000 daltons.

6 Claims, 9 Drawing Sheets

ANTI-METASTATIC FACTOR

FIELD OF THE INVENTION

The present invention relates to a factor which inhibits the proliferation of tumor cells.

BACKGROUND OF THE INVENTION

Inhibition of the proliferation of tumor cells is one of the main purposes of the therapy, especially the chemotherapy, of cancerous growths. A particular aspect of such proliferation is the phenomenon whereby some cells of the tumor break off into the bloodstream and travel to other parts of the body, where they produce secondary tumors; this phenomenon is termed metastasis. As is well-known, while there are many tumor-inhibiting substances either in actual use, or which have potential use, in the chemotherapy of cancer, nevertheless the problem of cancer as a whole is far from a solution. Thus, any new contribution to the art of chemotherapy provides the medical profession with an additional tool with which to fight this disease. As will be seen from the following description, the present invention provides a substance of biological origin which is believed to be useful in this context.

SUMMARY OF THE INVENTION

It is an object of the present invention to provide a tumor cell proliferation inhibition factor. Another object of the invention is to provide a method for inhibiting the proliferation of tumor cells, especially in animals. Other objects of the present invention will be apparent from the description which follows.

The present invention accordingly provides a tumor cell proliferation inhibition factor isolable from at least one material selected from muscle tissue and muscle cell culture. This factor may be obtained by culturing cells separated from muscle tissue, and particularly from the supernatant of such culture. This factor may have a molecular weight substantially in the range of from 25,000 to 30,000 daltons. The muscle tissue may be, e.g., that of new-born rats.

The present invention also provides a method for inhibiting the proliferation of tumor cells, which comprises applying to a locus containing tumor cells, a tumor cell proliferation inhibition factor isolable from at least one material selected from muscle tissue and muscle cell culture, as well as a method for inhibiting the proliferation of tumor cells in animals, which comprises administering to animals containing tumor cells susceptible to proliferation, an effective tumor cell proliferation inhibitory dose of a tumor cell proliferation inhibition factor isolable from at least one material selected from muscle tissue and muscle cell culture. "Animals" is intended to include both human and non-human animals. For purposes of definition, it is to be noted that the term "proliferation" in the present specification and claims is intended to include metastasis, but is not limited thereto.

DETAILED DESCRIPTION OF THE INVENTION

Figure 1:
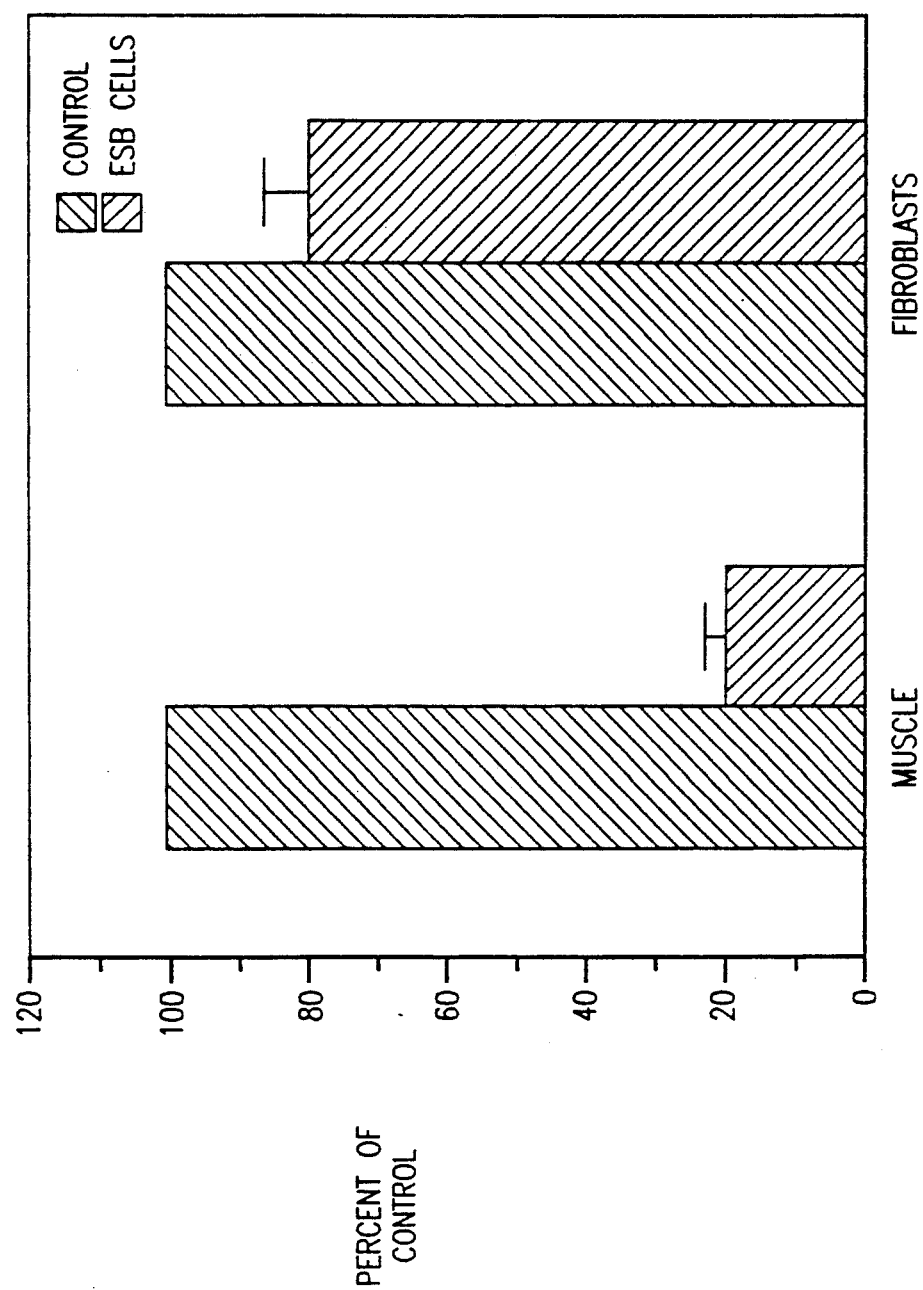
FIG. 1 illustrates the effect on ESB cells of muscle cells, in accordance with the invention.

It is presently preferred to isolate the factor of the present invention from muscle cells of newborn rats, more particularly from the supernatant when such cells are cultured. This does not of course exclude possible isolation of the factor from other sources. The presently preferred embodiments by which the factor according to the invention may be isolated and tested, are illustrated in the following non-limitative Example.

EXAMPLE

Materials and methods used for evaluation of inhibitory activity

Three tumor cell lines were used, namely, (1) ESB cells derived from a mouse lymphoma (see Schirrmacher V. et al, Int. J. Cancer 1979, 23: 233–244); (2) HT-29 cells derived from adenocarcinoma of the human colon, purchased from the American Type Culture Collection, Rockville, Md. U.S.A. (ATCC reference no. HTB-38); and (3) melanoma B-16 F1 cells (ATCC reference no. CRL 6323). All three types are known to metastasize after injection in rodents. The cells were routinely maintained in RPMI 1640 medium containing 10% fetal calf serum. Twice a week the cells were transferred to freshly prepared medium. The cells were examined 2 days following addition of fresh medium.

Fibroblasts, Strain IMR-90 (Science, 1977, 196: 60–63) were routinely maintained in RPMI medium containing 10% fetal calf serum. Twice a week the cells were transferred to freshly prepared medium. Supernatant was collected three days after passage.

Scanning Electron Microscopy was carried out according to well-known standard procedures, except for using plastic supports instead of cover glass slips, when adherent cells were examined.

Cell proliferation assays were carried out using 96 microwell plates. Cells were incubated with various media, detailed below, for 18 hours at 37° C. in an atmosphere containing 5% $CO_2$. At the end of the incubation period, each well was pulsed with 1 μl. of $^3$H TdR (New England Nuclear, Boston, Mass., U.S.A.) for the final 6 hours of culture. The pulsed cells were cultured and the amount of $^3$H TdR uptake was measured in a liquid scintillation counter.

Preparation of inhibitory factor

The muscles of the hind legs of 24–48 hour old newborn rats were separated and minced into small pieces. Following trypsinization with 0.25% trypsin-versan solution, the cells were preplated in tissue culture dishes for 30 minutes to remove the fibroblasts and monocytes. The cells were counted and seeded in enriched Dulbeco modified Eagle medium (DMEM). Five days later, the cultures contained contracting muscle cells. The medium was discarded and fresh RPMI medium with or without 10% fetal calf serum was added, and maintained for 24 hours. The supernatant was collected, centrifuged, and kept at 20° C. until required. This supernatant product is referred to herein as "muscle supernatant". It has been found that muscle supernatant remained active after heating at 56° C. for 30 minutes.

Analysis of inhibitory factor

GF-HPLC using a system supplied by Waters Associates (Milford, Mass., U.S.A.) was performed on the supernatant which was injected onto the column using a U6K injector. The system included two M-45 solvent delivery pumps, a M-721 solvent programmer and a model 481 variable wave-length detector. Separations were effected on a protein analysis I-125 column (300×7.8 cm.). Elution was carried out with PBS, pH 7.2, at a flow rate of 1 ml./min. and 1 ml. fractions were collected. Bovine serum albumin (67,000), ovalbumin (45,000), chymotrypsinogen (24,000) and cytochrome C (12,000) were used as marker proteins. The column fractions were subsequently tested for their ability to inhibit proliferation of HTB-38 cells. The various fractions eluted from the column were tested on the CPC (see below) of HT-29 cells.

RESULTS (a) Scanning Electron Microscopy

Muscle cells cultured for 5 days were incubated with ESB and HT-29 cells in RPMI 1640 medium containing 10% fetal calf serum for 24 hours at 37° C. in an atmosphere containing 5% $CO_2$. ESB cells incubated in absence of muscle cell culture showed numerous villous projections on their surface, whereas in presence of muscle cell culture they showed severe membranal damage with loss of the microvilli, appearance of membrane holes, and buddings. HT-29 cells were characterized by their elongated shape, with numerous microvilli; they grew in colonies of 40-50 cells without contact between colonies. Following incubation with muscle cell culture, the HT-29 cells transformed into small aggregates without possibility of distinguishing the membranal contours. The microvilli appeared grossly damaged. Both ESB and HT-29 cells incubated with fibroblasts (IMR-90) did not show any membranal alterations. Muscle cells incubated with medium only, showed relatively smooth surfaces. Following incubation with ESB cells, small buddings appeared on their membrane. Muscle cells incubated with HT-29 cells did not show any ultra structural membranal alterations. Fibroblasts (IMR-90) incubated with ESB or HT-29 cells did not show any change in their membranal cell structure.

(b) Cell proliferation capacity (CPC)

Figure 2:
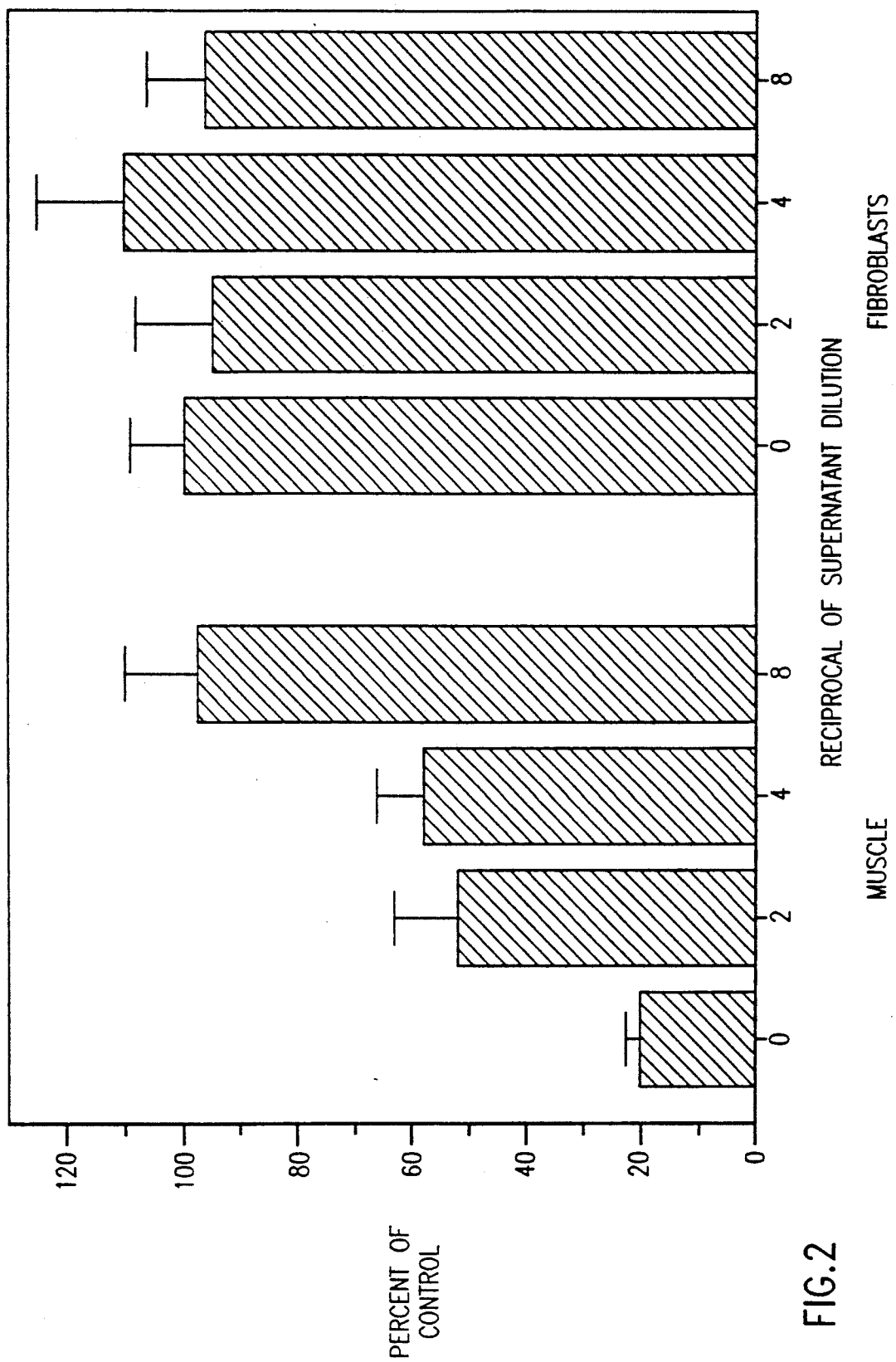
FIG. 2 illustrates the effect on ESB cells of muscle supernatant, in accordance with the invention.

FIG. 1 shows an 80% decrease in the proliferation capacity of ESB cells following incubation with muscle cells. Similar experiments with fibroblasts (IMR-90) caused a 20% decrease in CPC which was statistically insignificant. a dose dependent inhibition of the CPC (FIG. 2). The CPC of ESB cells incubated with fibroblast (IMR-90) supernatant did not show any difference from a similar experiment without supernatant.

Figure 3:
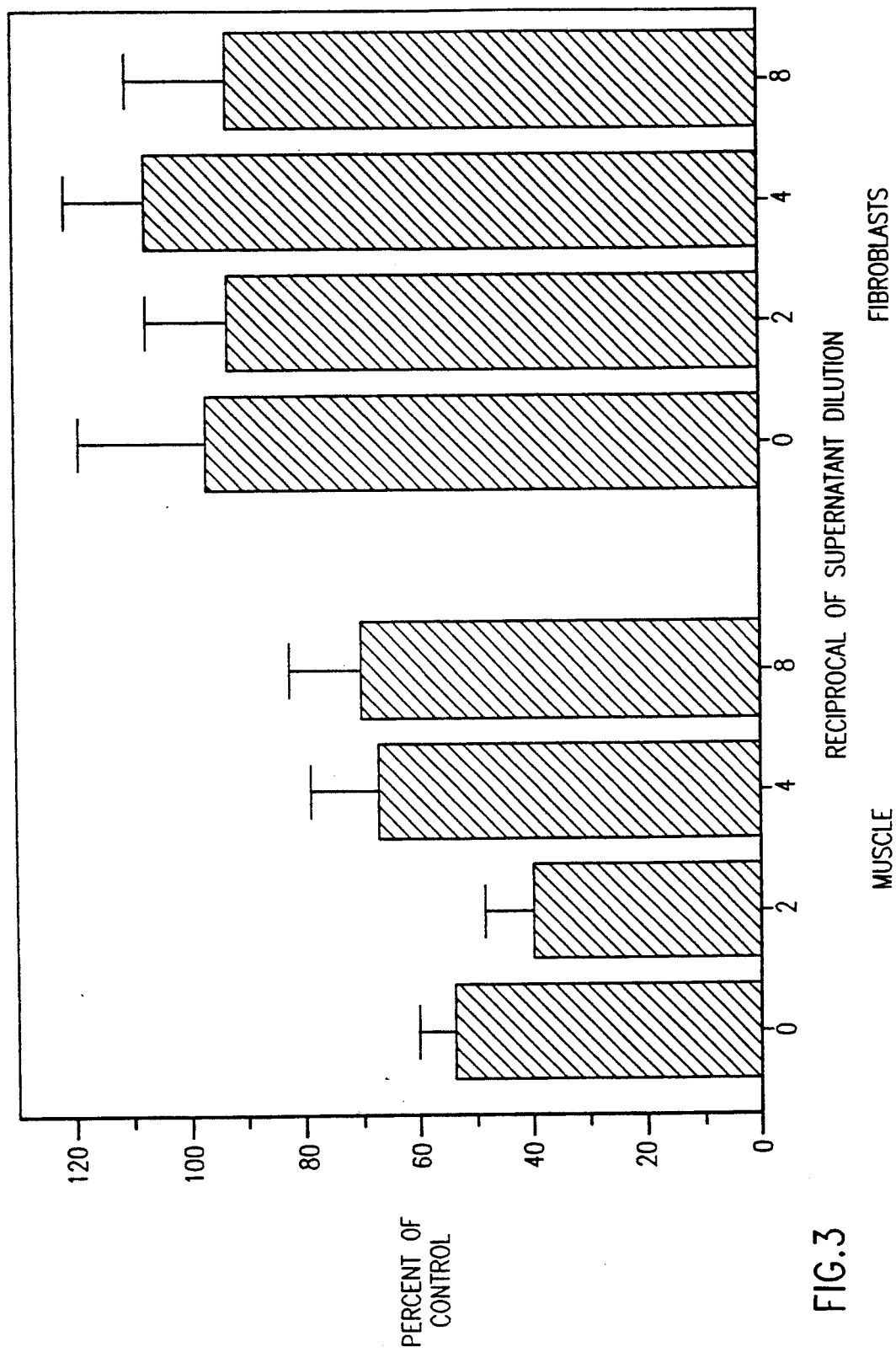
FIG. 3 illustrates the effect on HTB cells of the proliferation inhibition factor according to the invention.
Figure 4:
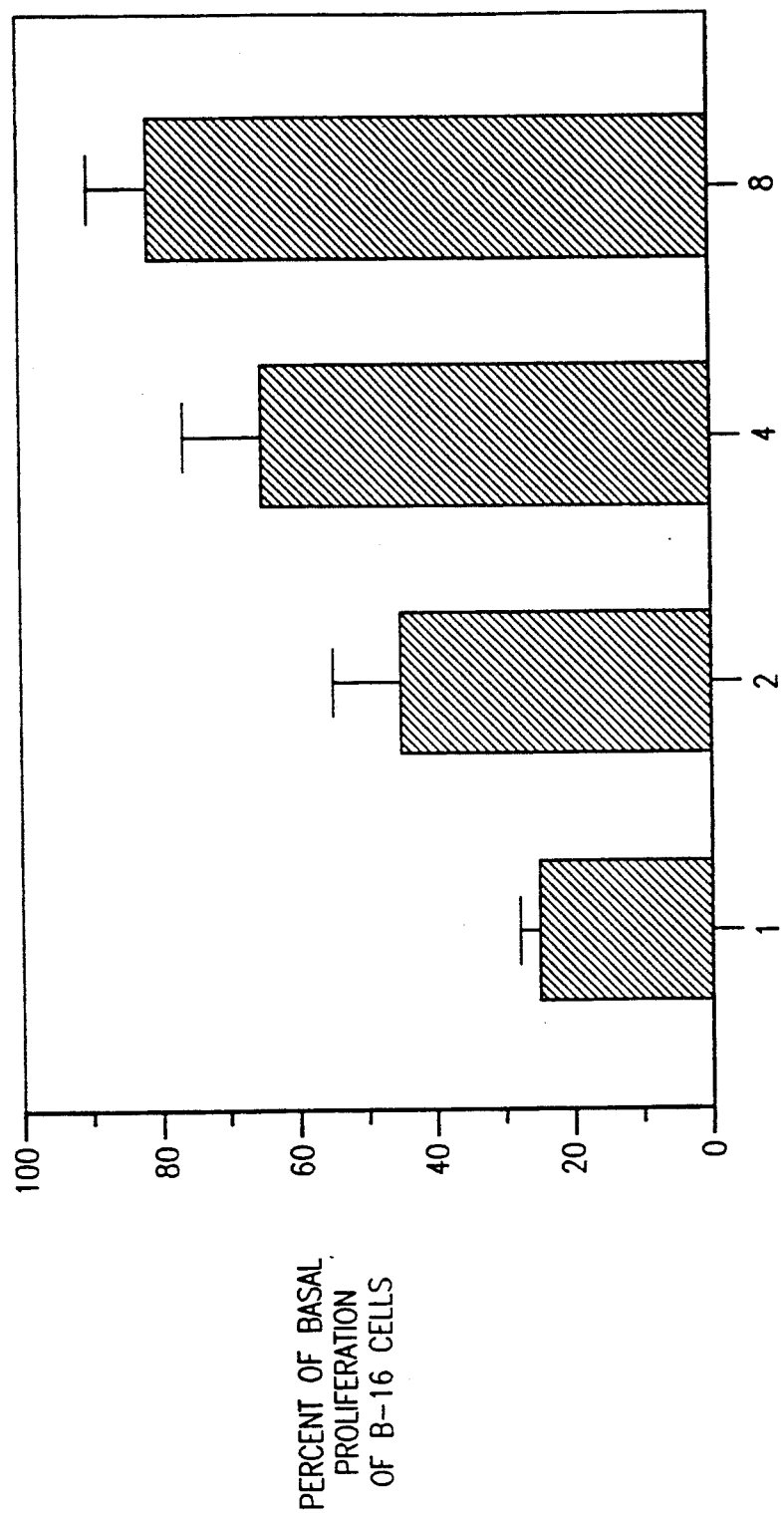
FIG. 4 illustrates the effect on B-16 F1 cells of the said proliferation inhibition factor.
Figure 5:
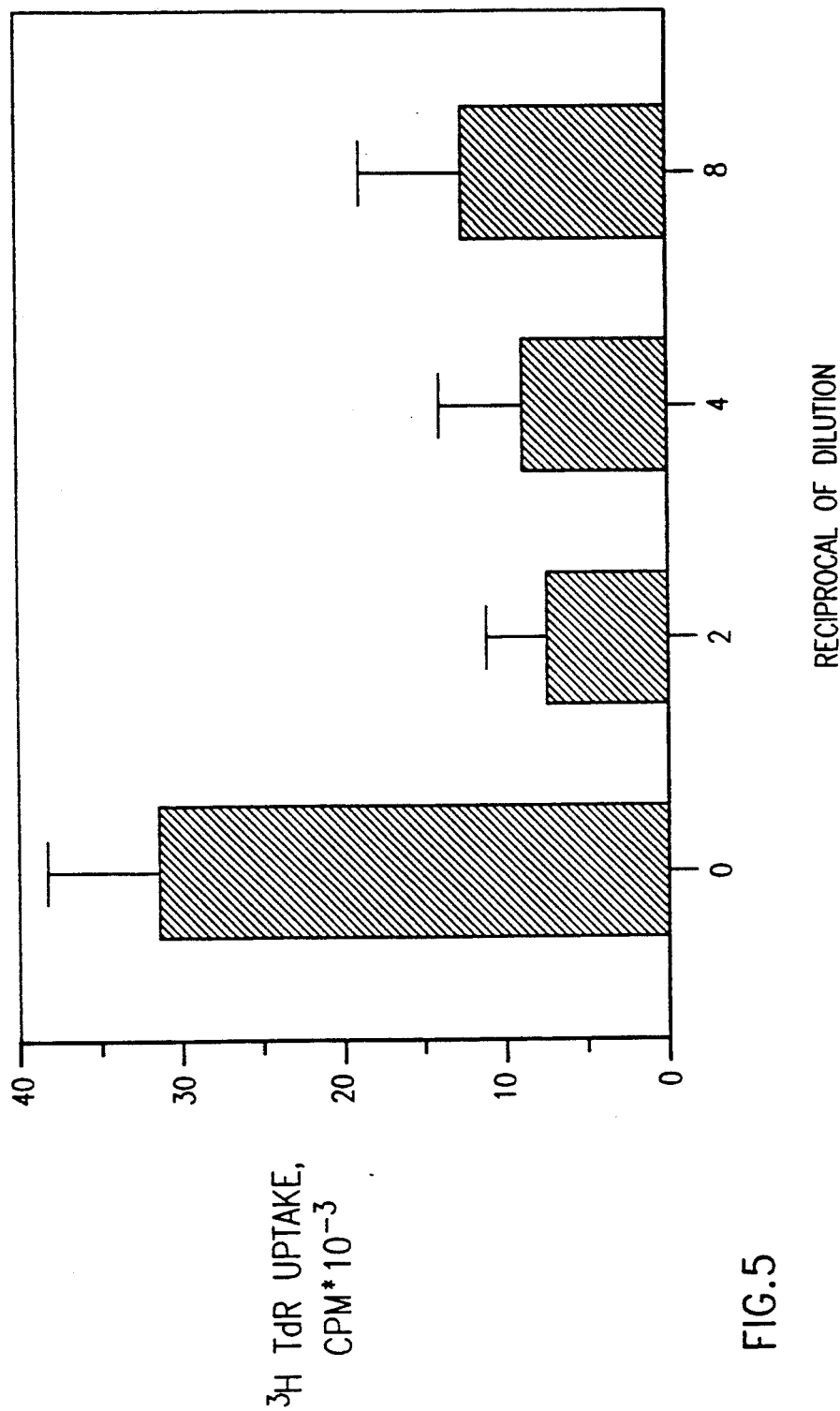
FIG. 5 illustrates the effect on CML cells of the said proliferation inhibition factor.

HT-29 cells incubated with muscle supernatant showed a dose dependent statistically significant inhibition of their CPC whereas cells incubated with the aforesaid fibroblast supernatant did not show any decrease in their CPC (FIG. 3). Melanoma B-16 F1 cells incubated with muscle supernatant also showed a dose dependent statistically significant inhibition of their CPC (FIG. 4). Moreover, it was found that muscle supernatant inhibited markedly the peripheral white blood cell proliferation of a patient with chronic myeloid leukemia (CML) (FIG. 5).

Figure 6:
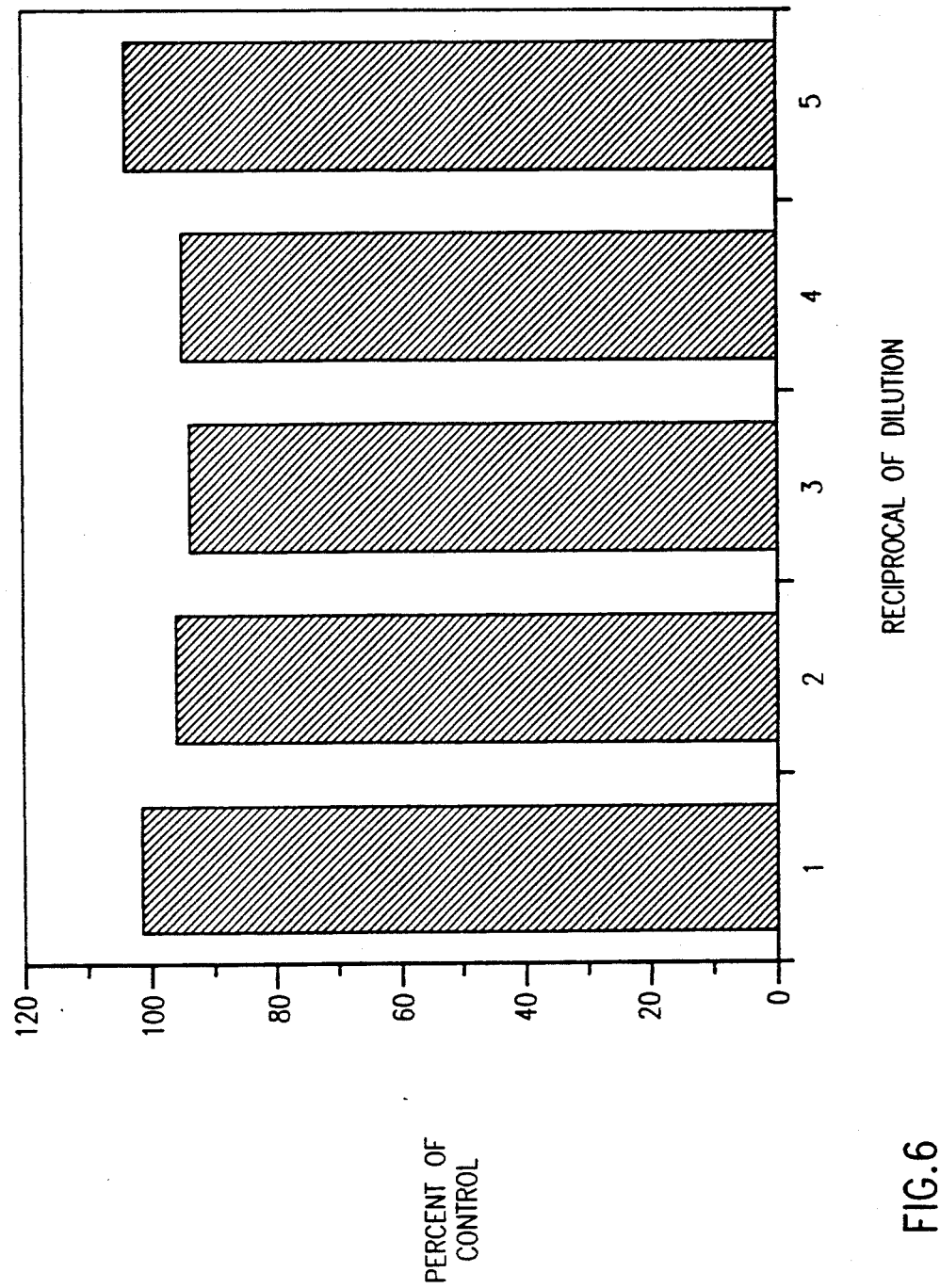
FIG. 6 illustrates the effect on human mononuclear cells of the said proliferation inhibition factor.

To examine the possibility that the present inhibitory factor affects only cells capable of proliferating, peripheral blood mononuclear cells obtained from healthy donors were incubated with muscle supernatant. In this case there was no effect on mononuclear reactive thymidine uptake (FIG. 6), although the counts obtained from these cells was relatively low, as expected (approximately 2000). This experiment showed that non-proliferating cells from healthy donors were substantially unaffected by the present inhibitory factor.

Figure 7:
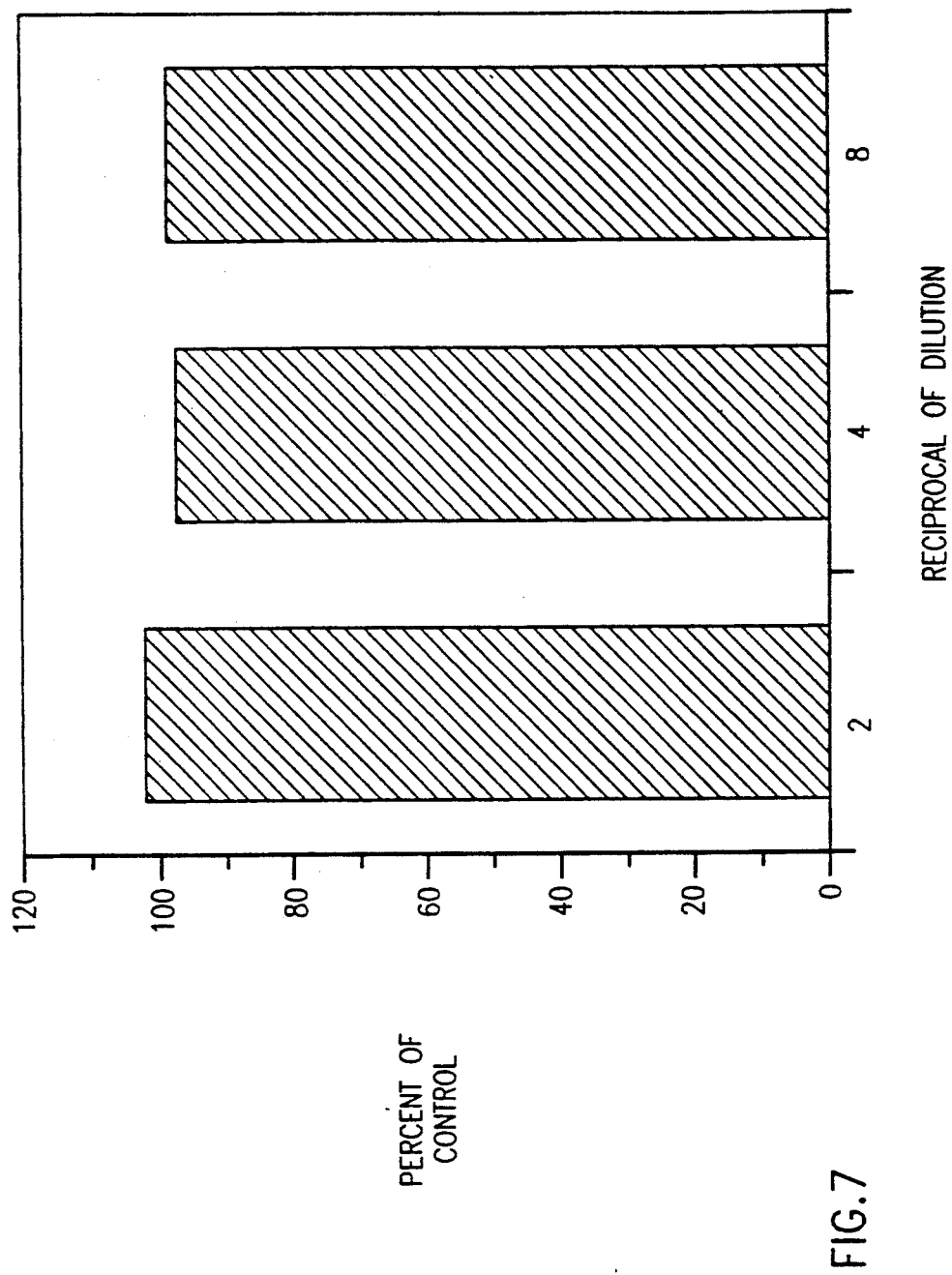
FIG. 7 illustrates the effect on mouse liver erythroblasts of the said proliferation inhibition factor.

Also, when the test was carried out with (proliferating) erythroid red cell precursors obtained from 11-day old mouse embryonic livers, no inhibitory effect on the cell CPC was observed (FIG. 7). This result appears to demonstrate that the inhibitory factor of the invention did not affect the proliferation of healthy cell precursors.

Figure 9:
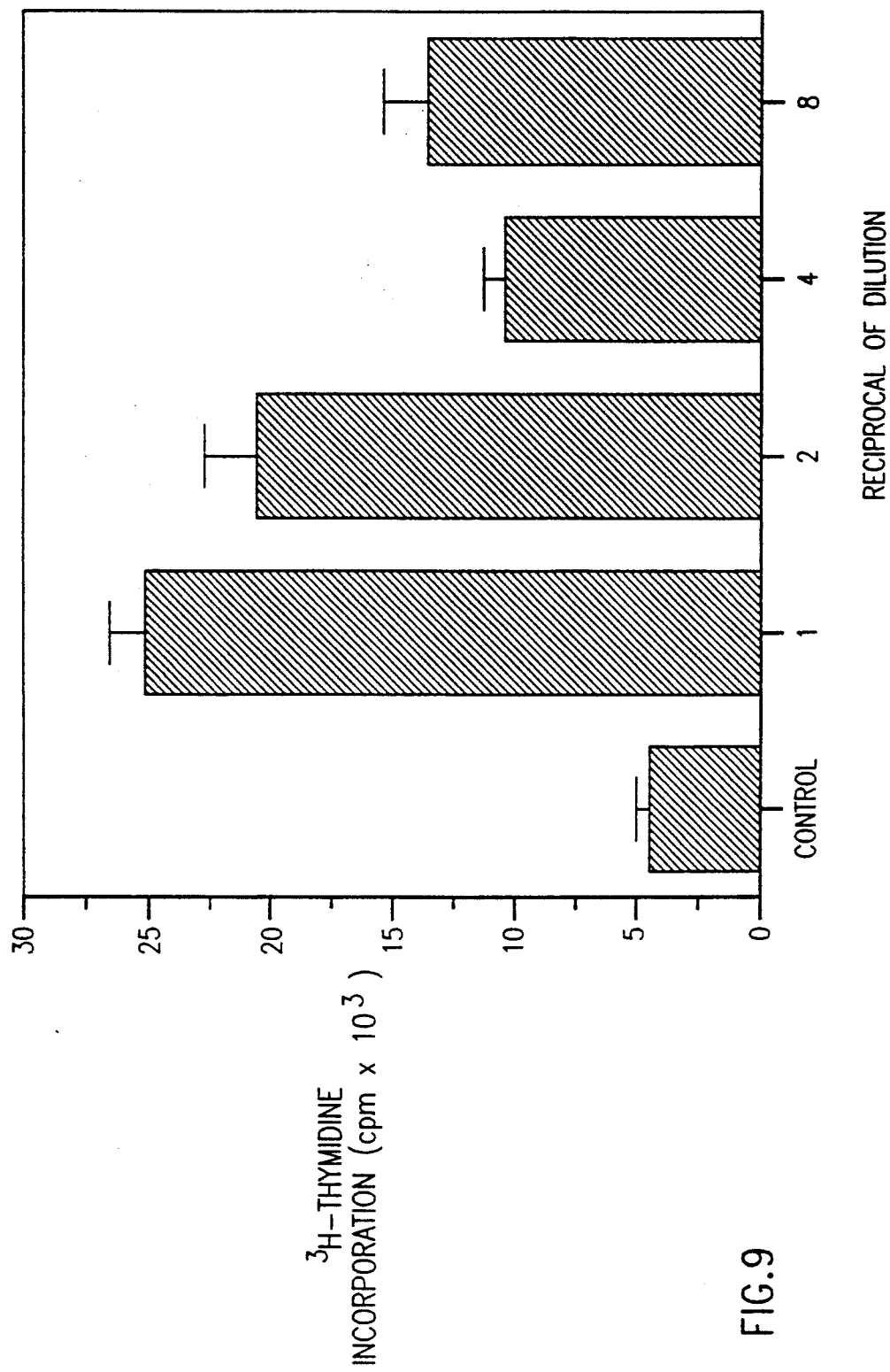
FIG. 9 illustrates the effect of muscle supernatants on the proliferation of normal mouse bone-marrow cells.

Similar results with even more pronounced stimulation of cell proliferation capacity were obtained when mouse bone-marrow cells were incubated with the muscle supernatants (see FIG. 9).

It will consequently be appreciated that the factor of the present invention has a definite advantage over the cytotoxic drugs presently used in the chemotherapy of cancer, insofar as these drugs generally depress bone marrow activity, whereas the present factor increases such activity.

(c) Fractionation of muscle supernatant

Figure 8:
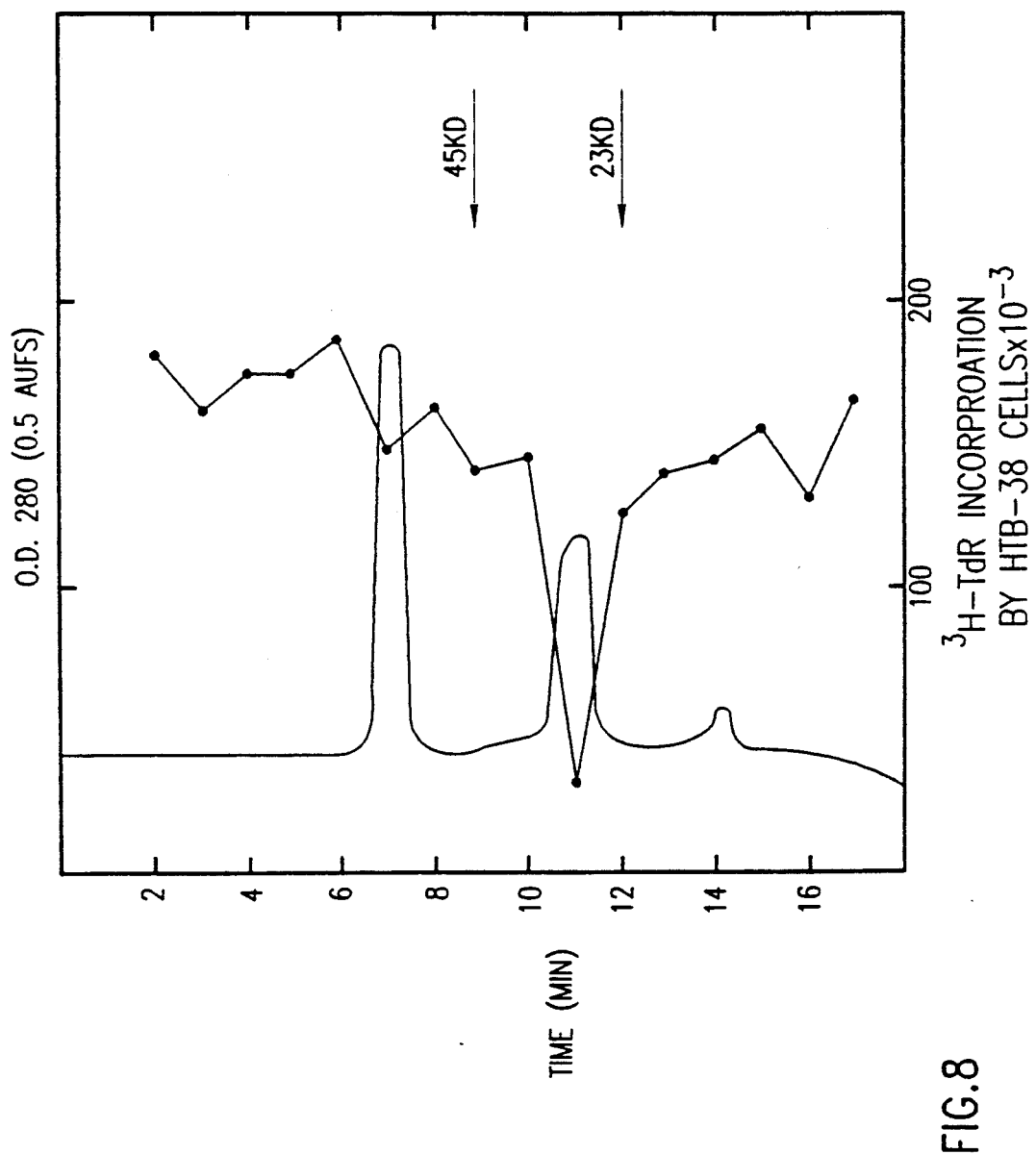
FIG. 8 illustrates molecular weight determination of the said proliferation inhibition factor.

Fraction number 11, isolated by GF-HPLC, inhibited the CPC of HT-29 cells and was compatible with a molecular weight of 25-30,000 daltons (FIG. 8).

(d) Comparison of muscle supernatant activity with other factors

Analysis of muscle supernatant showed that it possessed no IL-1, IL-2, or TNF activity. Moreover, recombinant CSF (mouse), IL-1 (human), IL-2 (human), IL-3 (human), IL-4 (human), IL-5 (mouse) and IL-6 (mouse) were found not to inhibit the proliferation of the ESB, HTB-38 or B-16 cell lines.

(e) In vivo studies with the muscle supernatant

C-57 BL 6J mice were injected intravenously with B-16 melanoma cells. Subsequently, intraperitoneal daily injections of 0.5 ml. muscle supernatant were administered. 18 days later the mice were sacrificed, the lungs were removed and the number of metastatic foci were counted. In the untreated mice, the number of such foci were approximately four times the number in the treated mice.

While the invention has been particularly described with respect to its presently preferred embodiments, it will be appreciated by persons skilled in the art that many modifications and variations may be made. Merely by way of example, skilled persons will appreciate that substances having the tumor cell proliferation inhibiting activity as herein described, but which may be isolated from parts of the body other than muscle tissue or muscle cells, are the obvious chemical equivalents of the factor described and claimed herein. Therefore, the invention is not to be construed as limited by such particularly described embodiments, rather its spirit and scope will be determined by reference to the claims which follow.

We claim:

1. A factor which selectively inhibits proliferation of malignant cells selected from the group consisting of leukemia, lymphoma, carcinoma and melanoma cells but which does not inhibit the proliferation of healthy cells which has a molecular weight as determined by GF-HPLC substantially in the range of from 25,000 to 30,000 daltons, and which is isolable from the liquid phase present in the culture system after culturing at least one material selected from the group consisting of straited muscle tissue, smooth muscle tissue, straited muscle cells and smooth muscle cells.

2. The factor according to claim 1, obtainable by culturing straited or smooth muscle cells isolated from straited or smooth muscle tissue.

3. The factor according to claim 1, wherein said muscle tissue and muscle cells are taken from newborn rats.

4. A method for selectively inhibiting proliferation of malignant cells selected from the group consisting of leukemia, lymphoma, carcinoma and melanoma cells, but without inhibiting the proliferation of healthy cells, in mammals, which comprises administering to mammals containing the malignant cells susceptible to proliferation, an amount of the factor as defined in claim 1 effective to inhibit the proliferation of the malignant cells.

5. The method according to claim 4, wherein said factor is obtainable by culturing straited or smooth muscle cells isolated from straited or smooth muscle tissue.

6. The method according to claim 4, wherein said muscle tissue is that of newborn rats.

* * * * *